United States Patent
Cole et al.

(10) Patent No.: US 7,671,079 B2
(45) Date of Patent: Mar. 2, 2010

(54) SULFONYLTETRAHYDRO-3H-BENZO(E)INDOLE-8-AMINE COMPOUNDS AS 5-HYDROXYTRYPTAMINE-6 LIGANDS

(75) Inventors: Derek Cecil Cole, New City, NY (US); Magda Asselin, Mahwah, NJ (US)

(73) Assignee: Wyeth LLC, Madison, NJ (US)

( * ) Notice: Subject to any disclaimer, the term of this patent is extended or adjusted under 35 U.S.C. 154(b) by 166 days.

(21) Appl. No.: 11/899,631

(22) Filed: Sep. 6, 2007

(65) Prior Publication Data
US 2008/0085925 A1    Apr. 10, 2008

Related U.S. Application Data

(62) Division of application No. 10/984,633, filed on Nov. 9, 2004, now Pat. No. 7,288,561.

(60) Provisional application No. 60/519,063, filed on Nov. 10, 2003.

(51) Int. Cl.
*A61K 31/404* (2006.01)
*C07D 209/56* (2006.01)

(52) U.S. Cl. .................. 514/411; 548/427; 548/429
(58) Field of Classification Search .............. 548/427, 548/429; 514/411
See application file for complete search history.

(56) References Cited

U.S. PATENT DOCUMENTS

| | | | |
|---|---|---|---|
| 4,370,341 A | 1/1983 | Asselin et al. | |
| 4,454,150 A | 6/1984 | Asselin et al. | |
| 4,929,622 A | 5/1990 | Allen et al. | |
| 5,288,748 A | 2/1994 | Wikstrom et al. | |
| 5,302,599 A | 4/1994 | Ennis et al. | |
| 7,288,561 B2 * | 10/2007 | Cole et al. | 514/411 |

OTHER PUBLICATIONS

Lin, Chiu-Hong et al., *Journal of Heterocyclic Chemistry*, 1994, 31:129-139.
Ennis, Michael D., et al., *Journal of Medicinal Chemistry*, 1995, 38:2217-2230.

* cited by examiner

*Primary Examiner*—Golam M Shameem
(74) *Attorney, Agent, or Firm*—Thomas C. McKenzie

(57) ABSTRACT

The present invention provides a compound of formula I and the use thereof in the therapeutic treatment of a CNS disorder related to or affected by the 5-HT6 receptor.

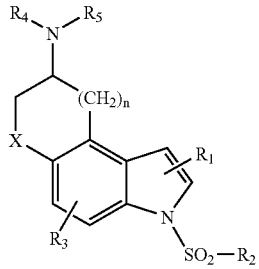

(I)

13 Claims, No Drawings

SULFONYLTETRAHYDRO-3H-BENZO(E)INDOLE-8-AMINE COMPOUNDS AS 5-HYDROXYTRYPTAMINE-6 LIGANDS

This application is a divisional of co-pending application Ser. No. 10/984,633 filed on Nov. 9, 2004, which claims priority from U.S. provisional application Ser. No. 60/519,063, filed Nov. 10, 2003, each application is hereby incorporated by reference in its entirety.

BACKGROUND OF THE INVENTION

Serotonin (5-Hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

One potential therapeutic use of modulators of 5-HT6 receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; El Mestikawy, S. *Brain Research*, 1997, 746, 207-219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology,* 2000, 130(1), 23-26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680).

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, J. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY OF THE INVENTION

The present invention provides a compound of formula I

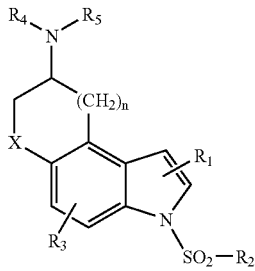

wherein

X is $CR_6R_7$, O or S;

n is an integer of 1 or 2;

$R_1$ is H, halogen, CN, CHO, $OR_9$ or a $C_1$-$C_6$alkyl, aryl or heteroaryl group each optionally substituted;

$R_2$ is an optionally substituted $C_1$-$C_6$alkyl, $C_3$-$C_7$cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S with the proviso that when X is $CH_2$ then $R_2$ must be other than 4-methylphenyl;

$R_3$ is H, halogen, CN, $OR_{19}$, $OCO_2R_{10}$, $CO_2R_{11}$, $CONR_{12}R_{13}$, $SO_xR_{14}$, $NR_{15}R_{16}$, $COR_{17}$, or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_4$ and $R_5$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_4$ and $R_5$ may be taken together with the atom to which they are attached to form an optionally substituted 5- to 7-membered ring optionally containing an additional heteroatom selected from O, N or S;

$R_6$ and $R_7$ are each independently H or an optionally substituted $C_1$-$C_6$alkyl group;

$R_9$, $R_{10}$, $R_{11}$, $R_{14}$, $R_{17}$, $R_{18}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$ and $R_{13}$ are each independently H or an optionally substituted $C_1$-$C_6$alkyl group or $R_{12}$ and $R_{13}$ may be taken together with the atom to which they are attached to form a 5- to 7-membered ring optionally containing another heteroatom selected from O, $NR_{18}$ or $SO_m$;

$R_{15}$ and $R_{16}$ are each independently H or an optionally substituted $C_1$-$C_4$alkyl group or $R_{15}$ and $R_{16}$ may be taken together with the atom to which they are attached to form a 5- to 7-membered ring optionally containing another heteroatom selected from O, $NR_{18}$ or $SO_m$; and x and m are each independently 0 or an integer of 1 or 2; or a stereoisomer thereof or a pharmaceutically acceptable salt thereof.

The present invention also provides methods and compositions useful in the treatment of central nervous system disorders.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders, for example see C. Reavill and D. C. Rogers, Current Opinion in Investigational Drugs, 2001, 2(1):104-109, Pharma Press Ltd.

Surprisingly, it has now been found that sulfonyltetrahydrobenzoindoleamine compounds of formula I demonstrate 5-HT6 affinity along with significant sub-type selectivity. Advantageously, said formula I compounds are effective therapeutic agents for the treatment of central nervous system (CNS) disorders associated with or affected by the 5-HT6 receptor. Accordingly, the present invention provides sulfonyldihydroimidazopyridinone compounds of formula I

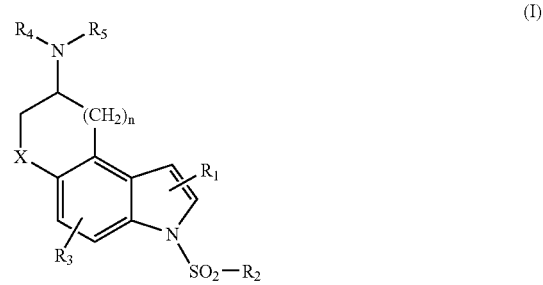

wherein

X is $CR_6R_7$, O or S;

n is an integer of 1 or 2;

$R_1$ is H, halogen, CN, CHO, $OR_9$ or a $C_1$-$C_6$alkyl, aryl or heteroaryl group each optionally substituted;

$R_2$ is an optionally substituted $C_1$-$C_6$alkyl, $C_3$-$C_7$cycloalkyl, aryl or heteroaryl group or an optionally substituted 8- to 13-membered bicyclic or tricyclic ring system having a N atom at the bridgehead and optionally containing 1, 2 or 3 additional heteroatoms selected from N, O or S with the proviso that when X is $CH_2$ then $R_2$ must be other than 4-methylphenyl;

$R_3$ is H, halogen, CN, $OR_{19}$, $OCO_2R_{10}$, $CO_2R_{11}$, $CONR_{12}R_{13}$, $SO_xR_{14}$, $NR_{15}R_{16}$, $COR_{17}$, or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_4$ and $R_5$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_4$ and $R_5$ may be taken together with the atom to which they are attached to form an optionally substituted 5- to 7-membered ring optionally containing an additional heteroatom selected from O, N or S;

$R_6$ and $R_7$ are each independently H or an optionally substituted $C_1$-$C_6$alkyl group;

$R_9$, $R_{10}$, $R_{11}$, $R_{14}$, $R_{17}$, $R_{18}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$ and $R_{13}$ are each independently H or an optionally substituted $C_1$-$C_6$alkyl group or $R_{12}$ and $R_{13}$ may be taken together with the atom to which they are attached to form a 5- to 7-membered ring optionally containing another heteroatom selected from O, $NR_{18}$ or $SO_m$;

$R_{15}$ and $R_{16}$ are each independently H or an optionally substituted $C_1$-$C_4$alkyl group or $R_{15}$ and $R_{16}$ may be taken together with the atom to which they are attached to form a 5- to 7-membered ring optionally containing another heteroatom selected from O, $NR_{18}$ or $SO_m$; and x and m are each independently 0 or an integer of 1 or 2; or a stereoisomer thereof or a pharmaceutically acceptable salt thereof.

As used in the specification and claims, the term halogen designates F, Cl, Br or I and the term cycloheteroalkyl designates a five- to seven-membered cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein X' is NR, O or S; and R is H or an optional substituent as described hereinbelow:

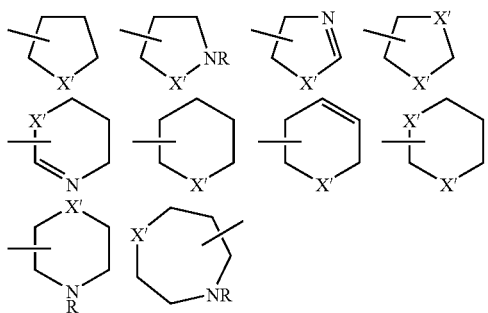

Similarly, as used in the specification and claims, the term heteroaryl designates a five- to ten-membered aromatic ring system containing 1, 2 or 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolyl, benzothienyl, benzofuranyl, benzisoxazolyl or the like. The term aryl designates a carbocyclic aromatic ring system such as phenyl, naphthyl, anthracenyl or the like. The term haloalkyl as used herein designates a $C_nH_{2n+1}$ group having from one to 2n+1 halogen atoms which may be the same or different and the term haloalkoxy as used herein designates an $OC_nH_{2n+1}$ group having from one to 2n+1 halogen atoms which may be the same or different.

Exemplary of the 8- to 13-membered bicyclic or tricyclic ring systems having a N atom at the bridgehead and optionally containing 1, 2 or 3 additional heteroatoms selected from N, O or S included in the term as designated herein are the following ring systems wherein W is NR, O or S; and R is H or an optional substituent as described hereinbelow:

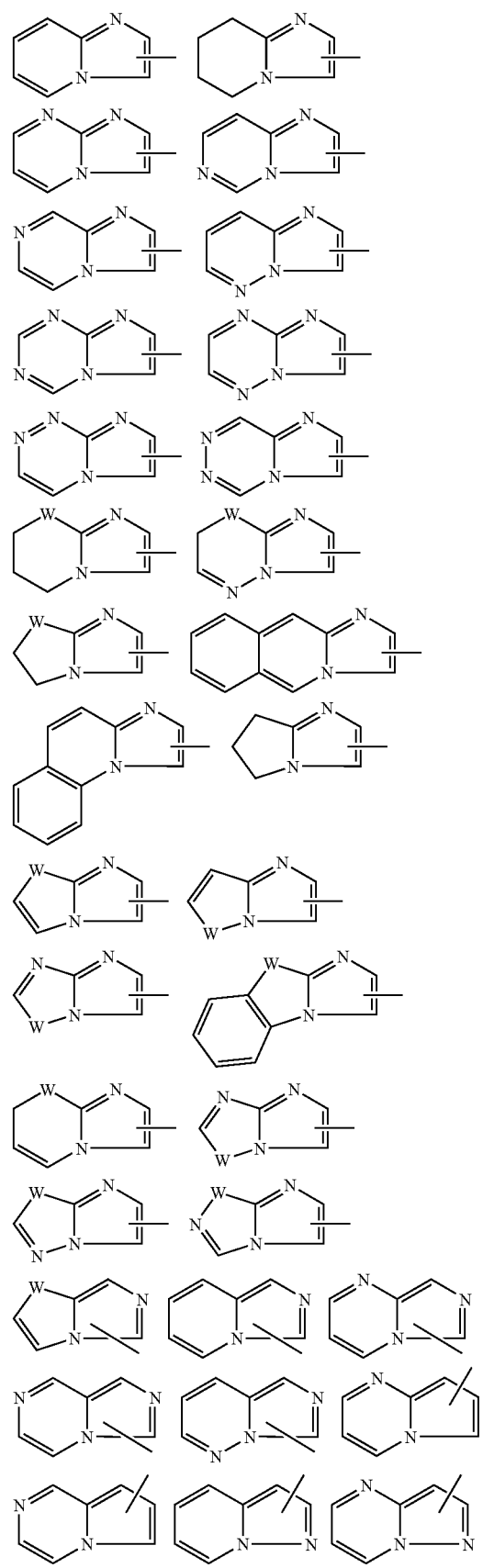

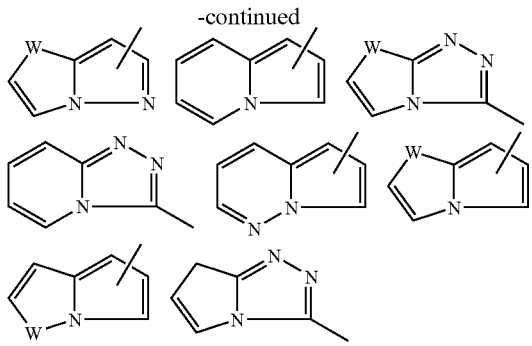

In the specification and claims, when the terms $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl are designated as being optionally substituted, the substituent groups which are optionally present may be one or more of those customarily employed in the development of pharmaceutical compounds, or the modification of such compounds, to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylaminocarbonyl, phenyl, phenoxy, benzyl, benzyloxy, heteroaryl, indolyl, heterocyclyl or cycloalkyl groups, preferably halogen atoms or lower alkyl or lower alkoxy groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein X is $CR_6R_7$. Another group of preferred compounds of the invention are those formula I compounds wherein n is 1. Also preferred are those compounds of formula I wherein $R_2$ is an optionally substituted aryl or heteroaryl group or an optionally substituted 8- to 13-membered bicyclic or tricyclic ring system having a N atom at the bridgehead and optionally containing 2 or 3 additional heteroatoms selected from N, O or S.

More preferred compounds of the invention are those compounds of formula I wherein X is $CR_6R_7$ and $R_6$ and $R_7$ are H. Another group of more preferred compounds are those compounds of formula I wherein X is $CH_2$ and $R_2$ is an optionally substituted phenyl or imidazothiazolyl group.

Among the preferred compounds of the invention are:
N,N-dimethyl-3-(phenylsulfonyl)-6,7,8,9-tetrahydro-3H-benzo[e]indol-8-amine;
N,N-dimethyl-3-(2-naphthylsulfonyl)-6,7,8,9-tetrahydro-3H-benzo[e]indol-8-amine;
3-[(4-fluorophenyl)sulfonyl]-N,N-dimethyl-6,7,8,9-tetrahydro-3H-benzo[e]indol-8-amine;
3-[(3,4-difluorophenyl)sulfonyl]-N,N-dimethyl-6,7,8,9-tetrahydro-3H-benzo[e]indol-8-amine;
3-[(2-chlorophenyl)sulfonyl]-N,N-dimethyl-6,7,8,9-tetrahydro-3H-benzo[e]indol-8-amine;
3-[(3-chlorophenyl)sulfonyl]-N,N-dimethyl-6,7,8,9-tetrahydro-3H-benzo[e]indol-8-amine;
3-[(2,3-dichlorophenyl)sulfonyl]-N,N-dimethyl-6,7,8,9-tetrahydro-3H-benzo[e]indol-8-amine;
3-[(2,4-diflorophenyl)sulfonyl]-N,N-dimethyl-6,7,8,9-tetrahydro-3H-benzo[e]indol-8-amine;
3-[(6-chloroimidazo[2,1-b][1,3]thiazol-5-yl)sulfonyl]-N,N-dimethyl-6,7,8,9-tetrahydro-3H-benzo[e]indol-8-amine;
3-[(2,6-dichloroimidazo[2,1-b][1,3]thiazol-5-yl)sulfonyl]-N,N-dimethyl-6,7,8,9-tetrahydro-3H-benzo[e]indol-8-amine;
N-methyl-3-(phenylsulfonyl)-6,7,8,9-tetrahydro-3H-benzo[e]indol-8-amine;
N-methyl-3-[(2-chlorophenyl)sulfonyl]-6,7,8,9-tetrahydro-3H-benzo[e]indol-8-amine;
3-(phenylsulfonyl)-6,7,8,9-tetrahydro-3H-benzo[e]indol-8-amine;
N,N-dimethyl-7-(phenylsulfonyl)-2,3,4,7-tetrahydro-1H-pyrrolo[2,3-h]quinolin-2-amine;
N,N-dimethyl-7-(phenylsulfonyl)-2,3,4,7-tetrahydropyrano[2,3-e]indol-2-amine;
N,N-dimethyl-7-(phenylsulfonyl)-2,3,4,7-tetrahydrothiopyrano[2,3-e]indol-2-amine;
N,N-dimethyl-7-[(2-chlorophenyl]sulfonyl)-2,3,4,7-tetrahydro-1H-pyrrolo[2,3-h]-quinolin-2-amine;
N,N-dimethyl-7-[(6-chloroimidazo[2,1-b][1,3]thiazol-5-yl)sulfonyl]-2,3,4,7-tetrahydro-1H-pyrrolo[2,3-h]quinolin-2-amine;
N,N-dimethyl-7-[(2-chlorophenyl)sulfonyl]-2,3,4,7-tetrahydropyrano[2,3-e]indol-2-amine;
N,N-dimethyl-7-[(6-chloroimidazo[2,1-b][1,3]thiazol-5-yl)sulfonyl]-2,3,4,7-tetrahydropyrano[2,3-e]indol-2-amine;
N,N-dimethyl-7-[(2-chlorophenyl)sulfonyl]-2,3,4,7-tetrahydrothiopyrano[2,3-e]indol-2-amine;
N,N-dimethyl-7-[(6-chloroimidazo[2,1-b][1,3]thiazol-5-yl)sulfonyl]-2,3,4,7-tetrahydrothiopyrano[2,3-e]indol-2-amine;
a stereoisomer thereof; or
a pharmaceutically acceptable salt thereof.

Advantageously, the present invention provides a process for the preparation of a compound of formula I which comprises reacting a compound of formula II with a sulfonyl chloride, $ClSO_2—R_2$, in the presence of a base, optionally in the presence of a solvent. The process is shown in flow diagram I.

FLOW DIAGRAM I

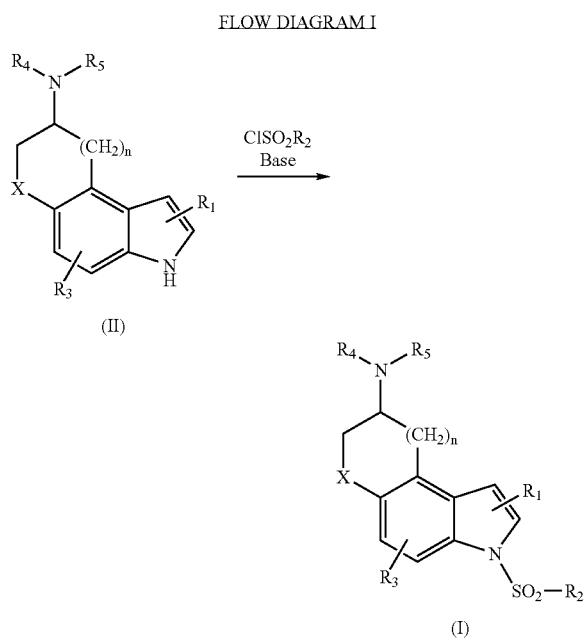

FLOW DIAGRAM II

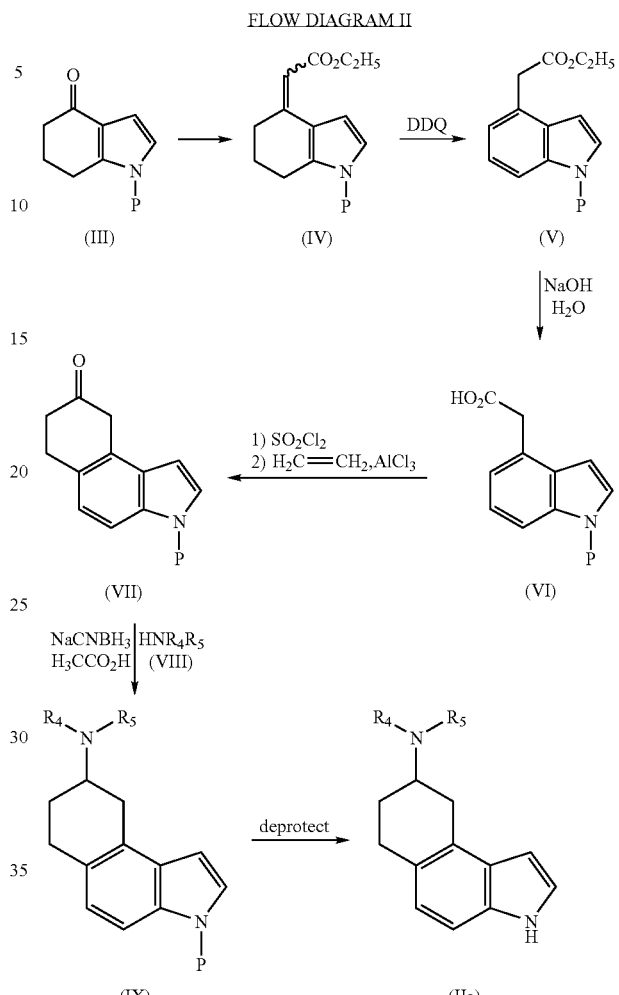

Bases suitable for use in the process of the invention include strong bases such as NaH, KOt-Bu, diisopropylethylamine, or any conventional base capable of removing a proton from a nitrogen atom.

Solvents suitable for use in the process of the invention include polar solvents such as tetrahydrofuran, dimethyl formamide, dimethylsulfoxide, lower alkyl alcohol, acetonitrile, or the like.

Compounds of formula II may be prepared using conventional synthetic methods and, if required, standard isolation or separation procedures. For example, compounds of formula II wherein X is $CH_2$; $R_1$ and $R_3$ are H; and n is 1 (IIa) may be prepared according to the method described by C. Lin et al. in J. Heterocyclic Chemistry (1994), 31, 129-139; i.e., by reacting a protected tetrahydroindol-4-one of formula III with triethyl phosphonoacetate and NaH to give the compound of formula IV; reducing the formula IV compound with 2,3-dichloro-5,6-dicyano-1,4-benzoquinone (DDQ) in dioxane to give the ester of formula V; hydrolyzing said ester with NaOH in methanol/water to give the corresponding acid of formula VI; reacting said acid with thionyl chloride to give the corresponding acid chloride and reacting said acid chloride with ethylene and $AlCl_3$ to give the formula VII ketone; reacting said ketone with an amine of formula VIII under reductive amination conditions ($NaCNBH_3$/acetic acid/tetrahydrofuran-methanol) to give the protected compound of formula IX; and deprotecting said formula IX compound in the presence of an acid to give the desired compound of formula IIa. The reaction is shown in flow diagram II wherein P represents a protecting group.

Protecting groups suitable for use in the reactions shown hereinabove include p-toluenesulfonyl, t-butoxycarbonyl, benzyl, acetyl, benzyloxycarbonyl, or any conventional group known to protect a basic nitrogen in standard synthetic procedures.

Compounds of formula II wherein X is O or S; $R_1$ and $R_3$ are H; and n is 1 (IIb) may be prepared according to the method described in U.S. Pat. No. 5,288,748; i.e., reducing a 3-nitropyrano or -thiopyrano compound of formula X to give the corresponding 3-amino compound of formula XI, alkylating said 3-amino compound using standard sequential alkylation or reductive alkylation techniques to give the compound of formula XII; nitrating the formula XIII compound with fuming nitric acid and $H_2SO_4$ to give the 6-nitro compound of formula XIII; reducing the 6-nitro compound with zinc dust in acetic acid to give the 6-amino compound of formula XIV; reacting said formula XIV compound with chloral hydrate and hydroxylamine HCl to give the compound of formula XV; cyclizing the formula XV compound with $H_2SO_4$ to give the diketone compound of formula XVI; and reducing said diketone with $LiAlH_4$ to give the desired compound of formula IIb. The reaction is shown in flow diagram III wherein X is O or S and Hal represents Cl or Br.

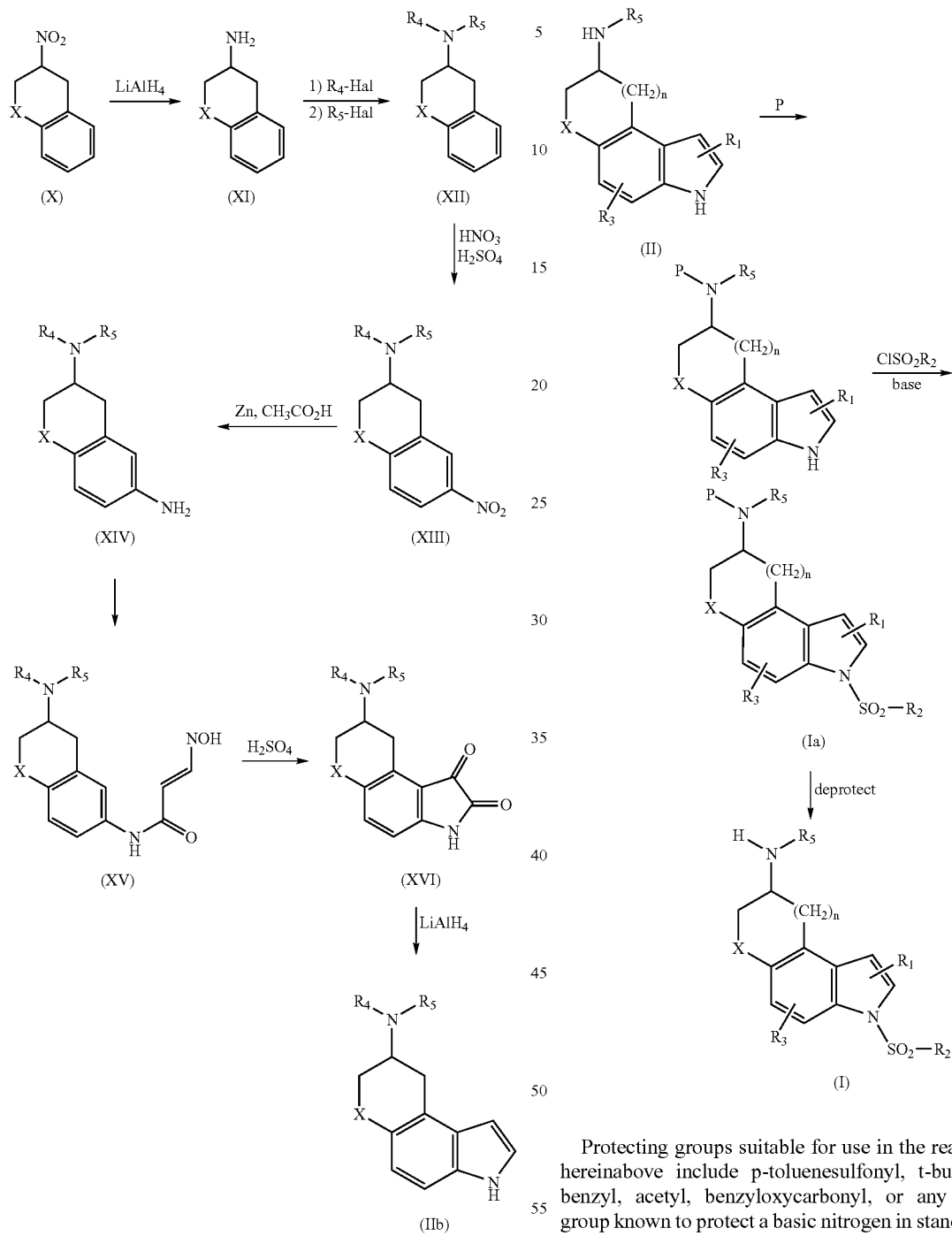

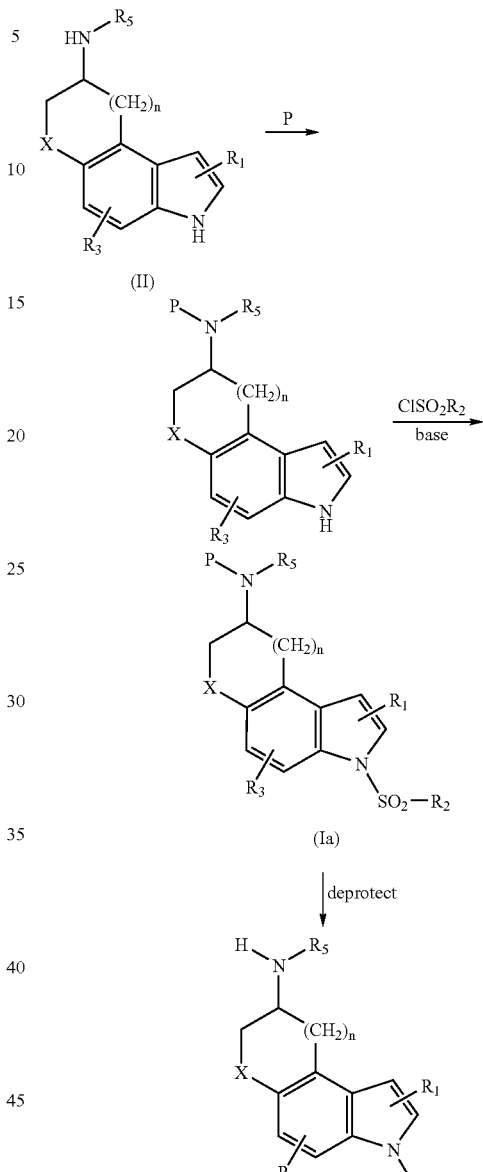

Compounds of formula II wherein $R_4$ or $R_5$ are H may be converted to compounds of formula I by first adding a protecting group, then sulfonylating as shown in flow diagram I to give the protected compound of formula Ia and deprotecting to give the desired compound of formula I. The reaction sequence is shown in flow diagram IV wherein P represents a protecting group. It is understood that either or both of $R_4$ and $R_5$ may be H.

Protecting groups suitable for use in the reactions shown hereinabove include p-toluenesulfonyl, t-butoxycarbonyl, benzyl, acetyl, benzyloxycarbonyl, or any conventional group known to protect a basic nitrogen in standard synthetic procedures.

Advantageously, the formula I compounds of the invention are useful for the treatment of CNS disorders relating to or affected by the 5-HT6 receptor including mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician or the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms HPLC and NMR designate high performance liquid chromatography and nuclear magnetic resonance, respectively. The terms DMSO and THF designate dimethylsulfoxide and tetrahydrofuran, respectively; and the term EtOAc designates ethyl acetate

EXAMPLE 1

Preparation of Ethyl {1-[(4-Methylphenyl)sulfonyl]-1,5,6,7-tetrahydro-4H-indol-4-ylidene}acetate

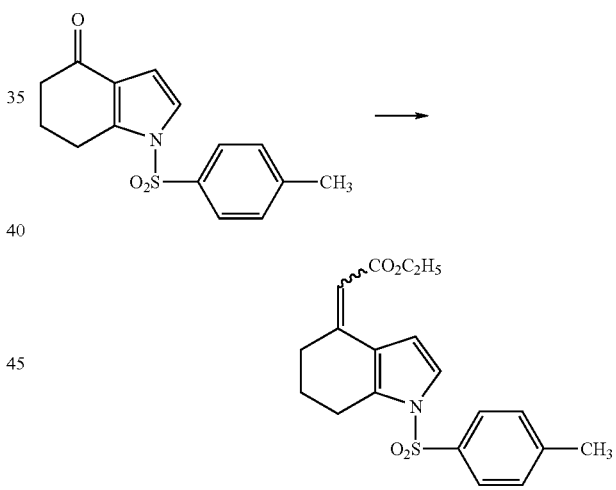

A mixture of 1-[(4-methylphenyl)sulfonyl]-1,5,6,7-tetrahydro-1H-indol-4-one (7.33 g, 25.3 mmol) in toluene under nitrogen is treated with NaH (60% in mineral oil, 1.31 g, 32.8 mmol), stirred for 5 min., treated dropwise with triethylphosphonoacetate (9.08 g, 40.5 mmol) over a 10 min. period, heated at reflux temperature for 18 h, cooled to room temperature and partitioned between ethyl acetate and water. The phases are separated and the aqueous phase is further extracted with ethyl acetate. The organic phases are combined, washed with water, dried over MgSO$_4$ and concentrated in vacuo. The resultant residue is chromatographed (silica gel, 25% ethyl acetate in hexane as eluent) to afford the title compound as a colorless oil, 6.41 g (70% yield), identified by NMR and mass spectral analyses.

EXAMPLE 2

Preparation of Ethyl 1-{[(4-Methylphenyl)sulfonyl]-1H-indol-4-yl}acetate

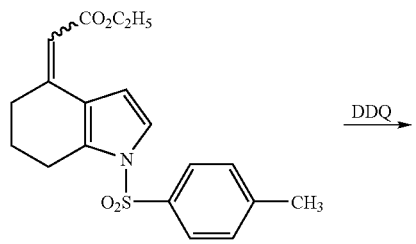

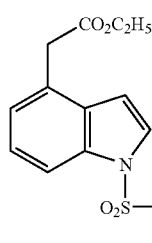

A solution of ethyl {1-[(4-methylphenyl)sulfonyl]-1,5,6,7-tetrahydro-4H-indol-4-ylidene}acetate (359 mg, 1.0 mmol in dioxane under nitrogen is treated with a solution of dichlorodicyanoquinone (DDQ) (341 mg, 1.5 mmol) in dioxane, heated at reflux temperature with stirring for 31 h, cooled to room temperature and concentrated in vacuo. The resultant residue is chromatographed (silical gel, 25% ethyl acetate in hexanes as eluent) to afford the title compound as a red-brown gum, 175 mg (49% yield). identified by NMR and mass spectral analyses.

EXAMPLE 3

Preparation of 1-{[(4-Methylphenyl)sulfonyl]-1H-indol-4-yl}acetic Acid

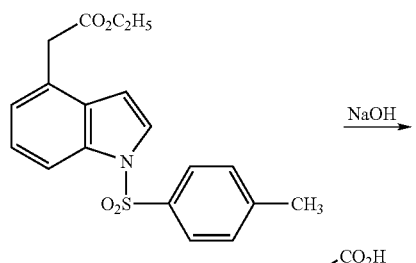

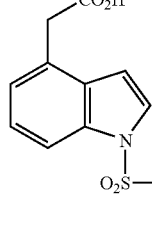

A solution of ethyl 1-{[(4-methylphenyl)sulfonyl]-1H-indol-4-yl}acetate (16.99 g, 47.5 mmol) in methanol is treated with 5N NaOH (36.7 mL), stirred under nitrogen for 4 h, concentrated in vacuo to remove the methanol, acidified with 6N HCl and extracted with ethyl acetate. The extracts are combined, washed with water, dried over MgSO$_4$ and concentrated in vacuo. The resultant residue is chromatographed (silical gel, 50% ethyl acetate in hexanes as eluent) to afford the title compound as a light brown glass, 14.13 g (90% yield), identified by mass spectral analyses.

EXAMPLE 4

Preparation of 3-[(4-Methylphenyl)sulfonyl]-6,7,8,9-tetrahydro-3H-benzo[e]indol-8-one

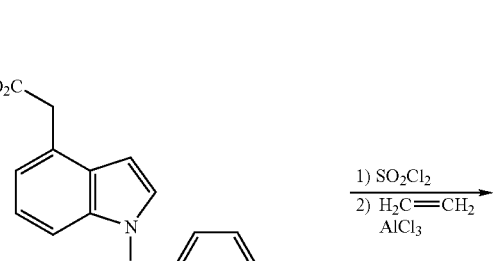

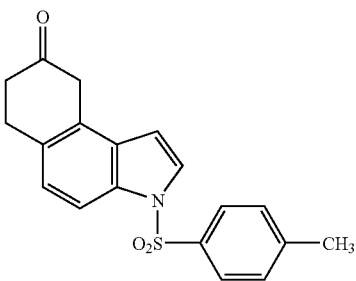

A solution of 1-{[(4-methylphenyl)sulfonyl]-1H-indol-4-yl}acetic acid (498 mg, 1.51 .mmol) in CH$_2$Cl$_2$ it treated with thionyl chloride (0.225 mL, 3.09 mmol) under nitrogen, stirred for 2 h and concentrated to dryness in vacuo. The resultant residue is dissolved in CH$_2$Cl$_2$ and reevaporated. The process is repeated to remove the excess thionyl chloride. The final oil residue is dissolved in CH$_2$Cl$_2$ and added dropwise over a 15 minute period at −20° C. to a stirred mixture of AlCl$_3$ in CH$_2$Cl$_2$ which has been presaturated with ethylene gas. The reaction mixture is stirred and bubbled with ethylene gas at −20° C. for 1 h, poured onto ice and extracted with CH$_2$Cl$_2$. The extracts are combined, washed with water, dried over MgSO$_4$ and concentrated in vacuo. This residue is chromatographed (silica gel, CH$_2$Cl$_2$ as eluent) to afford the title compound as beige crystals, 215 mg (42% yield), identified by NMR and mass spectral analyses.

EXAMPLE 5

Preparation of N,N-Dimethyl-3{[(4-methylphenyl)sulfonyl]-6,7,8,9-tetrahydro-3H-benzo[e]indol-8-yl}amine

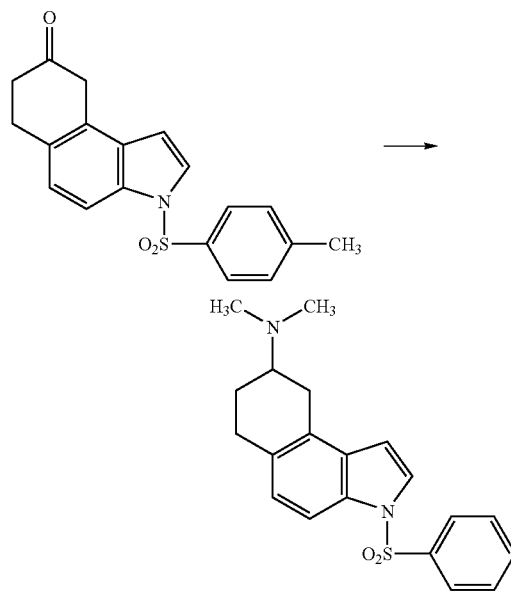

A solution of 3-[(4-methylphenyl)sulfonyl]-6,7,8,9-tetrahydro-3H-benzo[e]indol-8-one (0.10 g, 0.73 mmol) 0.295 mmol) in THF is treated sequentially with 2M dimethyl amine in THF (3 mL), sodium triacetoxyborohydride (0.28 g) and, acetic acid, stirred at room temperature for 5 days, quenched with water and extracted with ether The aqueous phase is basified with 1N NaOH and extracted with ether. These extracts are combined, dried over $MgSO_4$ and concentrated in vacuo to afford the title product as a semi-solid, 35 mg, (14% yield), identified by NMR and mass spectral analyses.

EXAMPLE 6

Preparation of N-(Cyclopropylmethyl)-3-[(4-methylphenyl)sulfonyl]-6,7,8,9-tetrahydro-3H-benzo[e]indol-8-amine

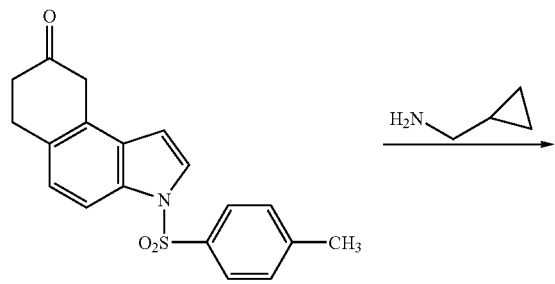

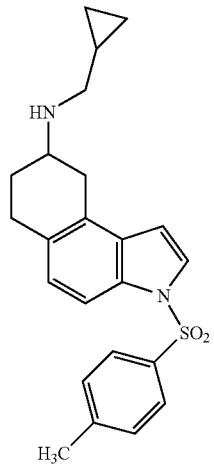

A solution of 3-[(4-methylphenyl)sulfonyl]-6,7,8,9-tetrahydro-3H-benzo[e]indol-8-one (2.0 g) in $CH_2Cl_2$ is treated sequentially with aminomethylcyclopropane ((0.630 g, 1.5 eq.) and sodium triacetoxyborohydride (1.6 g, 1.3 eq.), stirred at room temperature for 16 h, quenched with 1N NaOH and extracted with $CH_2Cl_2$. The extracts are combined, dried over $MgSO_4$ and concentrated in vacuo to give the title product, 2.2 g, identified by NMR and mass spectral analyses.

EXAMPLE 7

Preparation of N,N-Dimethyl-6,7,8,9-tetrahydro-3H-benzo[e]indol-8-amine

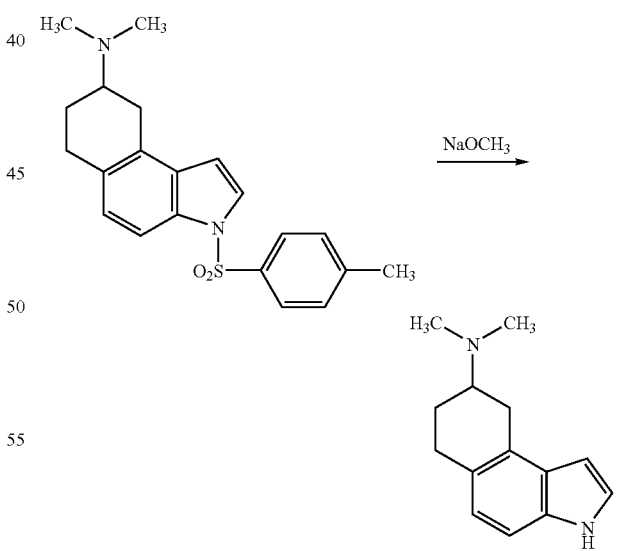

A solution of N,N-dimethyl-3{[(4-methylphenyl)sulfonyl]-6,7,8,9-tetrahydro-3H-benzo[e]indol-8-yl}amine (0.035 g) in a 1:1 mixture of methanol:THF is treated with 0.5 mL of $NaOCH_3$ (25% in methanol), heated at reflux temperature for 2 h, cooled and concentrated in vacuo. The resultant residue is diluted with water and extracted with EtOAc. The extracts are combined, dried over MgSO$_4$ and concentrated in vacuo to afford the title product, 0.015 g, identified by NMR and mass spectral analyses.

EXAMPLE 8

Preparation of N,N-Dimethyl-3-(Phenylsulfonyl)-6,7,8,9-tetrahydro-3H-benzo[e]indol-8-amine

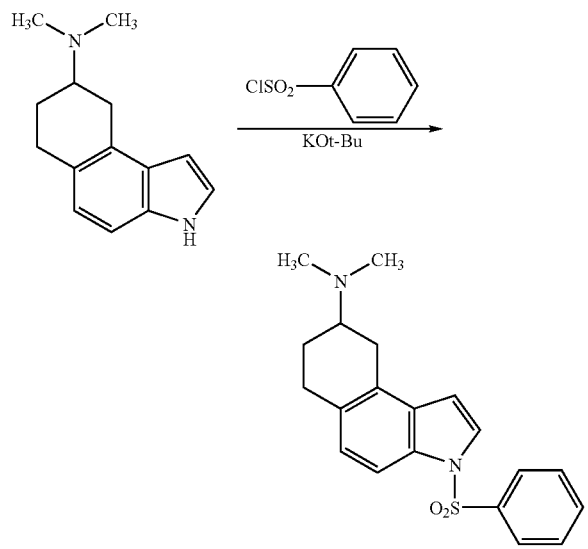

A solution of N,N-dimethyl-6,7,8,9-tetrahydro-3H-benzo[e]indol-8-amine (32 mg, 0.2 mmol) in THF is treated with benzenesulfonyl chloride (29.1 mg, 0.22 mmol) followed by KOtBu (19.8 mg, 0.22 mmol), stirred at room temperature for 18 h and concentrated in vacuo. The resultant residue is dissolved in a mixture of DMSO, methanol and water and purified by Gilson preparative HPLC[1] to give the title compound, [M+H] 369, retention time (RT) 2.067 minutes.

[1] Gilson Preparative HPLC conditions: Gilson Preparative HPLC system; YMC Pro C18, 20 mm×50 mm ID, 5 uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.

EXAMPLES 9-27

Preparation of N,N-Dimethyl-3-(arylsulfonyl)-6,7,8,9-tetrahydro-3H-benzo[e]indol-8-amine Compounds

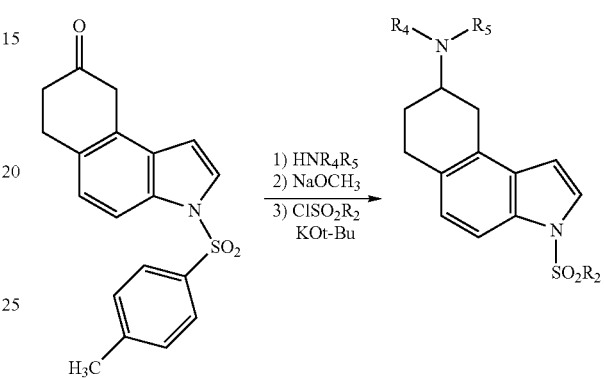

Using essentially the same procedures described in Examples 5-8 hereinabove and employing the appropriate amine and sulfonyl chloride reagents, the compounds shown on Table I are obtained and identified by HPLC[2] and mass spectral analyses.

[2] HPLC Conditions: HP 1100 HPLC system; Waters Xterra MS C18, 4.6 (i.d.)×50 mm, 3.5 μm, set at 40° C.; Flow rate 0.8 mL/min; Solvent A: 0.02% Formic Acid in water; Solvent B: 0.02% Formic Acid in ACN; Gradient: Time 0: 100% A; Time 1.0 min 100% A; 3.5 min 100% B; Time 5.0 min 100% B; Sample concentration: ~1.0 mg/mL; Injection volume: 10 μL; Detection: 230, 254 nm DAD.

TABLE I

| Ex. No. | R2 | R4 | R5 | [M + H] | RT (min) |
|---|---|---|---|---|---|
| 9 | 4-trifluoromethoxyphenyl | CH$_3$ | CH$_3$ | 439 | 3.02 |
| 10 | 2-naphthyl | CH$_3$ | CH$_3$ | 406 | 3.11 |
| 11 | 4-fluorophenyl | CH$_3$ | CH$_3$ | 373 | 3.00 |
| 12 | 2-chloro-4-(trifluoromethyl)phenyl | CH$_3$ | CH$_3$ | 457 | 3.10 |
| 13 | 3,4-difluorophenyl | CH$_3$ | CH$_3$ | 391 | 2.84 |
| 14 | 2-chlorophenyl | CH$_3$ | CH$_3$ | 389 | 2.86 |
| 15 | 3-chlorophenyl | CH$_3$ | CH$_3$ | 389 | 2.93 |
| 16 | 2,3-dichlorophenyl | CH$_3$ | CH$_3$ | 424 | 2.93 |
| 17 | 2,4-difluorophenyl | CH$_3$ | CH$_3$ | 391 | 2.89 |
| 18 | 6-chloroimidazo[2,1-b][1,3]thiazol-5-yl | CH$_3$ | CH$_3$ | 435 | 2.87 |
| 19 | 2,6-dichloroimidazo[2,1-b][1,3]thiazol-5-yl | CH$_3$ | CH$_3$ | 470 | 2.88 |
| 20 | 3,5-dimethylisoxazol-4-yl | CH$_3$ | CH$_3$ | 374 | 2.73 |
| 21 | 4-methylphenyl | H | cyclopropyl | 381 | 1.965 |

TABLE I-continued

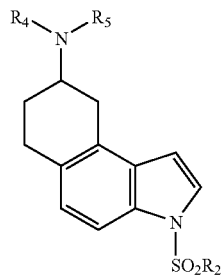

| Ex. No. | R2 | R4 | R5 | [M + H] | RT (min) |
|---|---|---|---|---|---|
| 22 | 4-methylphenyl | H | isopropyl | 384 | 2.116 |
| 23 | 4-methylphenyl | H | C$_4$H$_9$ | 398 | 2.216 |
| 24 | 4-methylphenyl | H | cyclobutyl | 395 | 1.99 |
| 25 | 4-methylphenyl | H | C$_3$H$_7$ | 383 | |
| 26 | 4-methylphenyl | H | CH$_3$ | 355 | 1.99 |
| 27 | 4-methylphenyl | C$_3$H$_7$ | C$_3$H$_7$ | 425 | 2.366 |

EXAMPLE 28

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM MgCl$_2$ and 0.5 mM EDTA and 20 μl of [$^3$H]-LSD (S.A., 86.0 Ci/mmol, available from Amersham Life Science), 3.0 nM. The dissociation constant, K$_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the IC$_{50}$ and the K$_i$ values of test compounds with 95% confidence limits. A linear regression line of data points is plotted, from which the IC$_{50}$ value is determined and the K$_i$ value is determined based upon the following equation:

$$K_i = IC_{50}/(1+L/K_D)$$

where L is the concentration of the radioactive ligand used and K$_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table II, below.

TABLE II

| Test Compound (Ex. No.) | 5-HT6 binding Ki (nM) |
|---|---|
| 8 | 1 |
| 9 | 79 |
| 10 | 13 |
| 11 | 19 |
| 12 | 55 |
| 13 | 9 |
| 14 | 2 |
| 15 | 2 |

TABLE II-continued

| | |
|---|---|
| 16 | 6 |
| 17 | 8 |
| 18 | 6 |
| 19 | 5 |
| 20 | 59 |
| 21 | 103 |
| 22 | 26 |
| 23 | 173 |
| 24 | 36 |
| 25 | 12 |
| 27 | 173 |

| Comparative Examples | 5-HT6 binding Ki |
|---|---|
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the data shown on Table II, the compounds of the invention demonstrate significant affinity for the 5-HT6 receptor site.

What is claimed is:

1. A method for the treatment of a central nervous system disorder related to or affected by the 5-HT6 receptor in a patient in need thereof which comprises providing to said patient a therapeutically effective amount of a compound of formula I

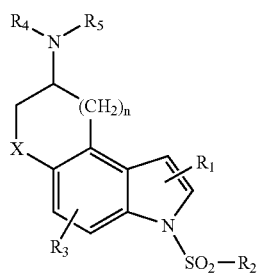

wherein

X is $CR_6R_7$, O or S;

n is an integer of 1 or 2;

$R_1$ is H, halogen, CN, CHO, $OR_9$, or a $C_1$-$C_6$alkyl, aryl or heteroaryl group each optionally substituted;

$R_2$ is an optionally substituted $C_1$-$C_6$alkyl, $C_3$-$C_7$cycloalkyl, aryl or heteroaryl group or an optionally substituted 8- to 13-membered bicyclic or tricyclic ring system having an N atom at the bridgehead and optionally containing 1, 2, or 3 additional heteroatoms selected form N, O, or S;

$R_3$ is H, halogen, CN, $OR_{19}$, $OCO_2R_{10}$, $CO_2R_{11}$, $CONR_{12}R_{13}$, $SO_xR_{14}$, $NR_{15}R_{16}$, $COR_{17}$, or a $C_1$-$C_6$alkyl, $C_2$-$C_6$alkenyl, $C_2$-$C_6$alkynyl, $C_3$-$C_7$cycloalkyl, aryl or heteroaryl group each optionally substituted;

$R_4$ and $R_5$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_4$ and $R_5$ may be taken together with the atom to which they are attached to form an optionally substituted 5- to 7-membered ring optionally containing an additional heteroatom selected from O, N, or S;

$R_6$ and $R_7$ are each independently H or an optionally substituted $C_1$-$C_6$alkyl group;

$R_9$, $R_{10}$, $R_{11}$, $R_{14}$, $R_{17}$, $R_{18}$ and $R_{19}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$ and $R_{13}$ are each independently H or an optionally substituted $C_1$-$C_6$alkyl group or $R_{12}$ and $R_{13}$ may be taken together with the atom to which they are attached to form a 5- to 7-membered ring optionally containing another heteroatom selected from O, $NR_{18}$, or $SO_m$;

$R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$, or $SO_m$; and x and m are each independently 0 or an integer of 1 or 2; or a stereoisomer thereof or a pharmaceutically acceptable salt thereof;

wherein the central nervous system disorder related to or affected by the 5-HT6 receptor is selected from the group consisting of an anxiety disorder; a cognitive disorder; attention deficit disorder; obsessive compulsive disorder; withdrawal from drug, alcohol or nicotine addiction; schizophrenia; depression; Alzheimer's disease; stroke; head trauma; and neuropathic pain.

2. The method according to claim 1 wherein said disorder is an anxiety disorder or a cognitive disorder.

3. The method according to claim 1 wherein said disorder is selected from the group consisting of: attention deficit disorder; obsessive compulsive disorder; withdrawal from drug, alcohol or nicotine addiction; schizophrenia; depression; and Alzheimer's disease.

4. The method according to claim 1 wherein said disorder is selected from the group consisting of: stroke; head trauma; and neuropathic pain.

5. A process for the preparation of a compound of formula I

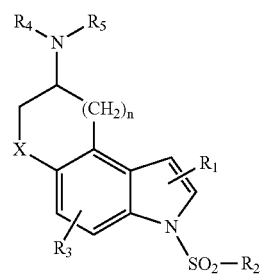

wherein

X is $CR_6R_7$, O or S;

n is an integer of 1 or 2;

$R_1$ is H, halogen, CN, CHO, $OR_9$, or a $C_1$-$C_6$alkyl, aryl or heteroaryl group each optionally substituted;

$R_2$ is an optionally substituted $C_1$-$C_6$alkyl, $C_3$-$C_7$cycloalkyl, aryl or heteroaryl group or an optionally substituted 8- to 13-membered bicyclic or tricyclic ring system having an N atom at the bridgehead and optionally containing 1, 2, or 3 additional heteroatoms selected form N, O, or S with the proviso that when X is CH2 then $R_2$ must be other than 4-methylphenyl;

$R_3$ is H, halogen, CN, $OR_{19}$, $OCO_2R_{10}$, $CO_2R_{11}$, $CONR_{12}R_{13}$, $SO_xR_{14}$, $NR_{15}R_{16}$, $COR_{17}$, or a C₁-C₆alkyl, C₂-C₆alkenyl, C₂-C₆alkynyl, C₃-C₇cycloalkyl, aryl or heteroaryl group each optionally substituted;

R₄ and R₅ are each independently H or a C₁-C₆alkyl, C₂-C₆alkenyl, C₂-C₆alkynyl, C₃-C₆cycloalkyl, cycloheteroalkyl, aryl or heteroaryl group each optionally substituted, or R₄ and R₅ may be taken together with the atom to which they are attached to form an optionally substituted 5- to 7-membered ring optionally containing an additional heteroatom selected from O, N, or S;

R₆ and R₇ are each independently H or an optionally substituted C₁-C₆alkyl group;

R₉, R₁₀, R₁₁, R₁₄, R₁₇, R₁₈ and R₁₉ are each independently H or a C₁-C₆alkyl, C₂-C₆alkenyl, C₂-C₆alkynyl, C₃-C₆cycloalkyl, cycloheteroalkyl, aryl or heteroaryl group each optionally substituted;

R₁₂ and R₁₃ are each independently H or an optionally substituted C₁-C₆alkyl group or R₁₂ and R₁₃ may be taken together with the atom to which they are attached to form a 5- to 7-membered ring optionally containing another heteroatom selected from O, NR₁₈, or SO_m;

R₁₅ and R₁₆ are each independently H or an optionally substituted C₁-C₄alkyl group or R₁₂ and R₁₃ may be taken together with the atom to which they are attached to form a 5- to 7-membered ring optionally containing another heteroatom selected from O, NR₁₈, or SO_m; and x and m are each independently 0 or an integer of 1 or 2 which process comprises reacting a compound of formula II

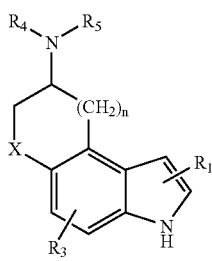

(II)

wherein X, n, R₁, R₃, R₄ and R₅, are as defined hereinabove with a sulfonyl chloride, ClSO₂R₂, in the presence of a base, optionally in the presence of a solvent.

6. The method of claim 1 wherein X is CR₆R₇.

7. The method of claim 1 wherein n is 1.

8. The method of claim 1 wherein R₂ is an optionally substituted aryl or heteroaryl group or an optionally substituted 8- to 13-membered bicyclic or tricyclic ring system having an N atom at the bridgehead and optionally containing 2 or 3 additional heteroatoms selected form N, O, or S.

9. The method of claim 6 wherein n is 1 and R₆ and R₇ are each H.

10. The method of claim 6 wherein R₄ and R₅ are each independently H or C₁-C₃alkyl.

11. The method of claim 9 wherein R₂ is an optionally substituted phenyl or imidazothiazolyl group.

12. The method of claim 11 wherein R₁ and R₂ are H and R₄ and R₅ are each independently H or CH₃.

13. The method of claim 1 wherein the compound of formula I is selected from the group consisting of:

N,N-dimethyl-3-(phenylsulfonyl)-6,7,8,9-tetrahydro-3H-benzo[e]indol-8-amine;

N,N-dimethyl-3-(2-naphthylsulfonyl)-6,7,8,9-tetrahydro-3H-benzo[e]indol-8-amine;

3-[(4-fluorophenyl)sulfonyl]-N,N-dimethyl-6,7,8,9-tetrahydro-3H-benzo[e]indol-8-amine;

3-[(3,4-difluorophenyl)sulfonyl]-N,N-dimethyl-6,7,8,9-tetrahydro-3H-benzo [e]indol-8-amine;

3-[(2-chlorophenyl)sulfonyl]-N,N-dimethyl-6,7,8,9-tetrahydro-3H-benzo[e]indol-8-amine;

3-[(3-chlorophenyl)sulfonyl]-N,N-dimethyl-6,7,8,9-tetrahydro-3H-benzo[e]indol-8-amine;

3-[(2,3-dichlorophenyl)sulfonyl]-N,N-dimethyl-6,7,8,9-tetrahydro-3H-benzo[e]indol-8-amine;

3-[2,4-difluorophenyl)sulfonyl]-N,N-dimethyl-6,7,8,9-tetrahydro-3H-benzo[e]indol-8-amine;

3-[(6-chloroimidazo[2,1-b][1,3]thiazol-5-yl)sulfonyl]-N,N-dimethyl-6,7,8,9-tetrahydro -3H-benzo[e]indol-8-amine;

3-[(2,6-dichloroimidazo[2, 1-b][1,3]thiazol-5-yl)sulfonyl]-N,N-dimethyl-6,7,8,9-tetrahydro-3H-benzo [e]indol-8-amine;

N-methyl-3-(phenylsulfonyl)-6,7,8,9-tetrahydro-3H-benzo[e]indol-8-amine;

N-methyl-3-[(2-chlorophenyl)sulfonyl]-6,7,8,9-tetrahydro-3H-benzo [e]indol-8-amine;

3-(phenylsulfonyl)-6,7,8,9-tetrahydro-3H-benzo[e]indol-8-amine;

N,N-dimethyl-7-(phenylsulfonyl)-2,3,4,7-tetrahydro-1 H-pyrrolo [2,3-h]quinolin-2-amine;

N,N-dimethyl-7-(phenylsulfonyl)-2,3,4,7-tetrahydropyrano[2,3-e]indol-2-amine;

N,N-dimethyl-7-(phenylsulfonyl)-2,3,4,7-tetrahydrothiopyrano[2,3-e]indol-2-amine;

N,N-dimethyl-7-[2-chlorophenyl)sulfonyl]-2,3,4,7-tetrahydro-1H-pyrrolo[2,3-h]-quinolin-2-amine;

N,N-dimethyl-7-[(6-chloroimidazo[2,1-b][1,3]thiazol-5-yl)sulfonyl]-2,3,4,7-tetrahydro -1 H-pyrrolo[2,3-h]-quinolin-2-amine;

N,N-dimethyl-7-[(2-chlorophenyl)sulfonyl]-2,3,4,7-tetrahydropyrano[2,3 -e]indol-2-amine;

N,N-dimethyl-7-[(6-chloroimidazo [2,1-b][1,3]thiazol-5-yl)sulfonyl]-2,3,4,7-tetrahydropyrano [2,3-e]-indol-2-amine;

N,N-dimethyl-7-[(2-chlorophenyl)sulfonyl]-2,3,4,7-tetrahydrothiopyrano[2,3-e]-indol-2-amine;

N,N-dimethyl-7-[(6-chloroimidazo[2,1-b][1,3]thiazol-5-yl)sulfonyl]-2,3,4,7-tetrahydrothiopyrano [2,3-e]-indol-2-amine;

a stereoisomer thereof; and a pharmaceutically acceptable salt thereof.

* * * * *